(12) United States Patent
Lakowicz

(10) Patent No.: US 6,432,637 B1
(45) Date of Patent: Aug. 13, 2002

(54) METHOD FOR DETERMINING A BASE SEQUENCE OF A NUCLEOTIDE STRAND

(76) Inventor: Joseph R. Lakowicz, 10037 Fox Den Rd., Ellicott City, MD (US) 21042

( * ) Notice: Subject to any disclaimer, the term of this patent is extended or adjusted under 35 U.S.C. 154(b) by 321 days.

(21) Appl. No.: 08/990,539

(22) Filed: Dec. 15, 1997

(51) Int. Cl.[7] .......................... C12Q 1/68; C12P 19/34; C07H 21/02; C07H 21/04

(52) U.S. Cl. .......................... 435/6; 435/6; 435/91.1; 435/91.2; 252/458.1; 252/519.13; 436/546; 536/23.1; 536/24.3; 536/24.31; 536/24.32; 536/24.33

(58) Field of Search .......................... 250/458.1; 435/6, 435/91.1, 91.2; 536/23.1, 24.3, 24.31, 24.32, 24.33; 436/546; 252/519.13; 556/136

(56) References Cited

U.S. PATENT DOCUMENTS 5,274,240 A * 12/1993 Mathies et al. .......... 250/458.1

FOREIGN PATENT DOCUMENTS

EP      340 605    *   4/1989

OTHER PUBLICATIONS

Zhang et al, "Use of Non–crosslinked polyacrylamide for four–color DNA sequencing by capillary electrophoresis separation of fragments up to 640 bases in length in two hours", Anal. Chem. 67:4589–4593, Dec. 1995.*

Bannwarth, "Bathophenanthroline–Ru(ll) complexes as nonradioactive labels for dideoxy DNA sequencing", Anal. Biochem. 181:216–219, 1989.*

Terpetschnig et al, "Fluorescence polarization immunoassay of a high molecular weight antigen using a long wavelength absorbing and laser diode excitable metal–ligand complex", Anal. Biochem. 250:54–59, Dec. 1996.*

Soper et al, "On–line fluorescence lifetime determinations in capillary electrophoresis", Anal. Chem. 67:4358–4365, Dec. 1995.*

* cited by examiner

*Primary Examiner*—Jeffrey Fredman
(74) *Attorney, Agent, or Firm*—Rothwell, Figg, Ernst & Manbeck

(57) ABSTRACT

A method for determining a base sequence of a nucleotide strand in a sample utilizes a probe including a fluorescent metal-ligand complex coupled to a first oligonucleotide having a sequence complementary to the first fragment of the strand. The first mixture is exposed to an exciting amount of radiation, and the fluorescence of the metal-ligand complex is detected. The first base sequence of the first fragment is identified based on fluorescence of the metal ligand complex. A second probe differing from the first by at least one base is provided. A second base of the second fragment is identified based on the fluorescence of the metal-ligand complex of the second probe. The second base sequence is compared to the first base sequence to identify a difference between the first and second sequences to determine a base sequence of the nucleotide strand.

17 Claims, 20 Drawing Sheets

Ru(bpy)₂(mi - phen)

[Ru(bpy)₂(mcsubpy)]⁺
or
[Ru(bpy)₂(mcbpy)]⁺

[Ru(bpy)₂ (dcsubpy)]
or
[Ru(bpy)₂(dcbpy)]

[Ru(bpy)₂ (phen - ITC)]²⁺
or
[Ru(bpy)₂(phen - NH)]²⁺

H

A

G-

τ = 2.3 μs
QY IN ACETONITRILE = 0.4
$\lambda_{EM}$ = 560 nm phen-ITC, 1,10-phenanthroline - 9 -isothiocyanate;

[Ru(dpp)$_2$(dcbpy)]$^{2+}$

[Ru(dpp)₂(mcbpy)]²⁺

[Ru(dpp(SO₃Na)₂)₂(dcbpy)]²⁺

[Ru(dpp(SO$_3$Na)$_2$)$_2$(mcbpy)]$^{2+}$

MOLECULAR STRUCTURE OF [Re(bcp)(CO)₃(4 - COOHPy)]⁺

Ru bis(2,2'-bipyridyl)(phenanthroline -maleamide)

mw = 688 g/mol

[Os(phen)$_2$(aphen)]$^{2+}$

[Os(tpy)(triphos)]$^{2+}$

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: cDNA (iv) ANTI-SENSE: NO (xi) SEQUENCE DESCRIPTION: SEQ ID NO:1:

CCCAGTCACG ACGTTGTAAA ACG      23

METHOD FOR DETERMINING A BASE SEQUENCE OF A NUCLEOTIDE STRAND

BACKGROUND OF THE INVENTION

1. Field of the Invention

The present invention is in the field of determining a base sequence of a nucleotide strand.

2. Description of the Background Art

The field of DNA sequencing is very active because of the decision to sequence the human genome. Presently available technology for determining a base sequence of a nucleotide strand uses different fluorescence labels on the four nucleotides, adenine, thymine, guanine, and cytosine, during sequencing. The nucleotide is identified by the emission spectrum which is distinct for each of the four probes used for each nucleotide.

The following references describe known DNA sequencing techniques which utilize measurement of fluorescence intensity:

T. Hunkapiller, R. J. Kaiser, B. F. Koop, and L. Hood, "Large-Scale and Automated DNA Sequence Determination," *Science* 254:59–67 (1991).

D. B. Shealy, M. Lipowska, J. Lipowski, N. Narayanan, S. Sutter, L. Strekowski, and G. Patonay, "Synthesis, Chromatographic Separation, and Characterization of Near-Infrared-Labeled DNA Oligomers for Use in DNA Sequencing," *Analytical Chemistry* 67:247–251 (1995).

J. Ju, C. Ruan, C. W. Fuller, A. N. Glazer, and R. A. Mathies, "Fluorescence energy transfer dye-labeled primers for DNA sequencing and analysis," *Biophysics* 92:4347–51 (1995).

J. Ju, A. N. Glazer, and R. A. Mathies, "Energy transfer primers: A new fluorescence labeling paradigm for DNA sequencing and analysis," *Nature Medicine* 2:246–49 (1996).

L. M. Smith, J. Z. Sanders, R. J. Kaiser, P. Hughes, C. Dodd, C. R. Connell, C. Heiner, S. B. H. Kent, and L. E. Hood, "Fluorescence detection in automated DNA sequence analysis," *Nature* 321:674–79 (1986).

D. C. Williams and S. A. Soper, "Ultrasensitive Near-IR Fluorescence Detection for Capillary Gel Electrophoresis and DNA Sequencing Applications," *Analytical Chemistry*, 67:3427–32.

S. Wiemann, J. Stegemann, D. Grothues, A. Bosch, X. Estivill, C. Schwager, J. Zimmermann, H. Voss, and W. Ansorge, "Simultaneous On-Line DNA Sequencing on Both Strands with Two Fluorescent Dyes," *Analytical Biochemistry* 224:117–21 (1995).

K. C. Huang, M. A. Quesada, and R. A. Mathies, "DNA Sequencing Using Capillary Array Electrophoresis," *Anal. Chem.* 64:2149–54 (1992).

J. M. Prober, G. L. Trainor, R. J. Dam, F. W. Hobbs, C. W. Robertson, R. J. Zagursky, A. J. Cocuzza, M. A. Jensen, and K. Baumeister, "A System for Rapid DNA Sequencing with Fluorescent Chain-Terminating Dideoxynucleotides," *Science* 238:336–41 (1987).

S. Takahashi, K. Murakami, T. Anazawa, and H. Kambara, "Multiple Sheath-Flow Gel Capillary-Array Electrophoresis for Multicolor Fluorescent DNA Detection," *Anal. Chem.* 66:1021–26 (1994).

The following references describe known DNA sequencing techniques which utilize measurement of fluorescence lifetime:

M. Sauer, K-T. Han, V. Ebert, R. Muller, A. Schulz, S. Seeger, J. Wolfrum, J. Arden-Jacob, G. Deltau, N. J. Marx, and K. H. Drexhage, "Design of Multiplex Dyes for the Detection of Different Biomolecules," 1994 SPIE Proc. 2137:762–774.

K-T. Han, M. Sauer, A. Schulz, S. Seeger, and J. Wolfrum, "Time-Resolved Fluorescence Studies of Labelled Nucleosides," *Ber. Busenges. Phys. Chem.* 97:1728–30 (1993).

K. Chang and R. K. Force, "Time-Resolved Laser-Induced Fluorescence Study on Dyes Used in DNA Sequencing," *Applied Spectroscopy* 47:24–29 (1993).

J. R. Lakowicz, H. Szmacinski, K. Nowaczyk, K. W. Berndt, and M. Johnson, "Fluorescence Lifetime Imaging," *Analytical Biochemistry* 202, 316–330 (1992).

The dyes described in the literature are based on near infrared probes, energy transfer probes to make the intensities equivalent, and other common fluorophores with visible excitation and emission wavelengths. None of these references mentions the use of metal-ligand complexes in determining a base sequence of a nucleotide strand.

The disadvantages of the currently available technology includes nanosecond decay times, which do not allow suppression of prompt auto-fluorescence, limited photostability, small Stoke's shifts and spectral overlap between the absorption and emission spectra.

In addition, with nanosecond decay times it is not possible to reject the auto-fluorescence from the samples, which is especially problematic with the low concentrations involved in the DNA sequencing. Furthermore, the use of nanosecond decay time fluorophores for sequencing based on the decay times, as has been proposed by other laboratories, requires complex instrumentation and is thus not likely to be widely utilized.

There is extensive literature regarding the spectral properties of metal-ligand complexes. The following is a list of papers regarding metal-ligand complexes:

Maestri, M., Sandrini, D., Balzani, V., Maeder, U. and von Zelewsky, "Absorption Spectra, Electrochemical Behavior, Luminescence Spectra, and Excited-State Lifetimes of Mixed-ligand Ortho-Metalated Rhodium(III) Complexes," *Inorg. Chem.*, 26:1323–1327(1987).

Sutin, N. and Creutz, C., "Properties and Reactivities of the Luminescent Excited States of Polypyridine Complexes of Ruthenium(II) and Osmium(II)," *Inorg. & Organometall. Photochem.*, Chap. 1, pp. 1–27 (1978).

Hager, G. D., Watts, R. J. and Crosby, G. A., "Charge-transfer Excited States of Ruthenium(II) Complexes. Relationship of Level Parameters to Molecular Structure," *J. Am. Chem. Soc.*, 97;7037–7042 (1975).

Orellana, G. and Braun, A. M., "Quantum Yields of $^3$MLCT Excited State Formation and Triplet-Triplet Absorption Spectra of Ruthenium(II) Tris-Chelate Complexes Containing Five- and Six-Membered Heterocyclic Moieties," *J. Photochem. Photobiol. A. Chem.*, 48:277–289 (1989).

Harrigan, R. W. and Crosby, G. A., "Symmetry Assignments of the Lowest CT Excited States of Ruthenium(II) Complexes Via a Proposed Electronic Coupling Model," *J. Chem. Phys.*, 59(7):3468–3476 (1973).

Yersin, H. and Braun, D., "Isotope-Induced Shifts of Electronic Transitions: Application to $[Ru(bpy-h_8)_3]^{2+}$ and $[Ru(bpy-d_8)_3]^{2+}$ in $[Zn(bpy-h_8)_3]$ $(ClO_4)_2$," *Chem. Phys. Letts.*, 179(1,2):85–94 (1991).

Coe, B. J., Thompson, D. W., Culbertson, C. T., Schoonover, J. R. and Meyer, T. J., "Synthesis and Photophysical Properties of Mono(2,2',2'-Terpyridine) Complexes of Ruthenium(II)," *Inorg. Chem.*, 34:3385–3395 (1995).

Lees, A. J., "Luminescence Properties of Organometallic Complexes," *Chem. Rev.,* 87:711–743 (1987).

DeArmond, M. K. and Carlin, C. M., "Multiple State Emission and Related Phenomena in Transition Metal Complexes," *Coordination Chem. Rev.,* 36:325–355 (1981).

Kondo, T., Yanagisawa, M. and Fujihira, M., "Single Exponential Decay for the Luminescence Intensity of Ru(bpy)$_3{}^{2+}$ Complex in Langmuir-Blodgett Films," *Chem. Letts.,* 1639–1993 (1993).

None of the above references suggest use of metal-ligand complexes in determining a base sequence of a nucleotide strand. Also, the use of metal-ligand complexes is not mentioned in the previous citations on fluorescence and DNA sequencing.

There remains a need in the art for improved methods of determining a base sequence of a nucleotide strand.

SUMMARY OF THE INVENTION

In accordance with the present invention, a method for determining a base sequence of a nucleotide strand in a sample includes the step of providing a first fragment of the strand. The emission from metal-ligand complexes may be from mixed singlet and triplet states. We will refer to the emission as fluorescence, though a more precise term may be luminescence. A fluorescent metal-ligand complex is coupled to a first oligonucleotide having a sequence complementary to the first fragment to form a first probe. The first probe is added to a sample that contains the first fragment to form a first mixture containing a first reaction product of the first probe and the first fragment. The first mixture is exposed to an exciting amount of radiation, and the fluorescence of the metal-ligand complex is detected. The first base sequence of the first fragment is identified based on fluorescence of the metal-ligand complex. A second fragment of the strand differing from the first fragment by at least one base is provided. A fluorescent metal-ligand complex is coupled to a second oligonucleotide having a sequence complementary to the second fragment to form a second probe. The second probe is added to a sample that contains the second fragment to form a second mixture containing a second reaction product of the second probe and the second fragment. The second mixture is exposed to an exciting amount of radiation, and the fluorescence of the metal-ligand complex is detected. A second base of the second fragment is identified based on the fluorescence of the metal-ligand complex. The second base sequence is compared to the first base sequence to identify a difference between the first and second sequences to determine a base sequence of the nucleotide strand.

Also in accordance with the present invention the combination of a first probe comprising a fluorescent metal-ligand complex coupled to a first oligonucleotide having a sequence complementary to a first fragment of a nucleotide strand and a second probe comprising a fluorescent metal-ligand complex coupled to a second oligonucleotide having a sequence complementary to a second fragment of the nucleotide strand differing from the first fragment by at least one base, for use in nucleotide sequencing.

DETAILED DESCRIPTION OF THE INVENTION

Figure 1:
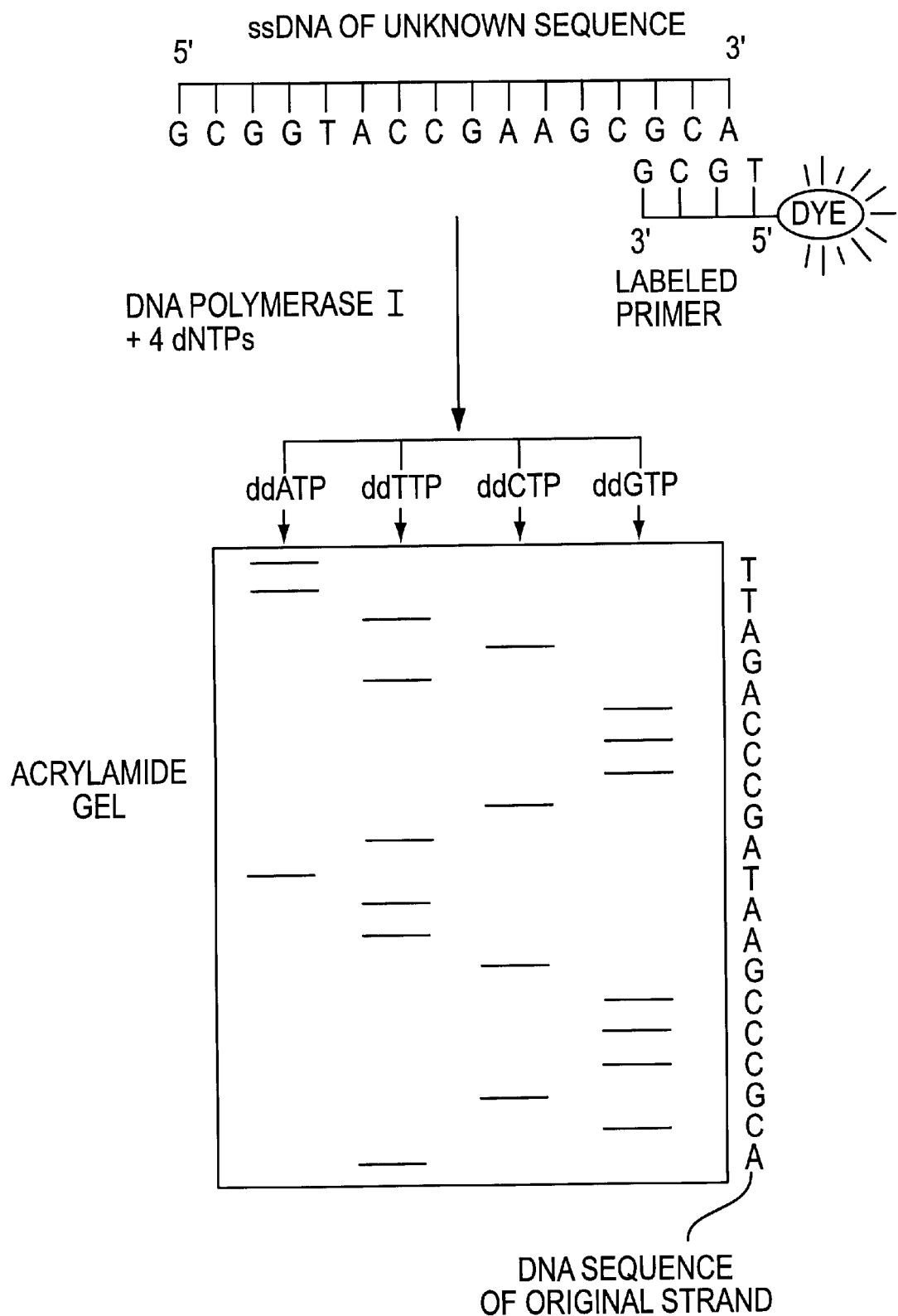
FIG. 1 graphically depicts DNA sequencing as accomplished by the dideoxy terminator method.
Figure 2:
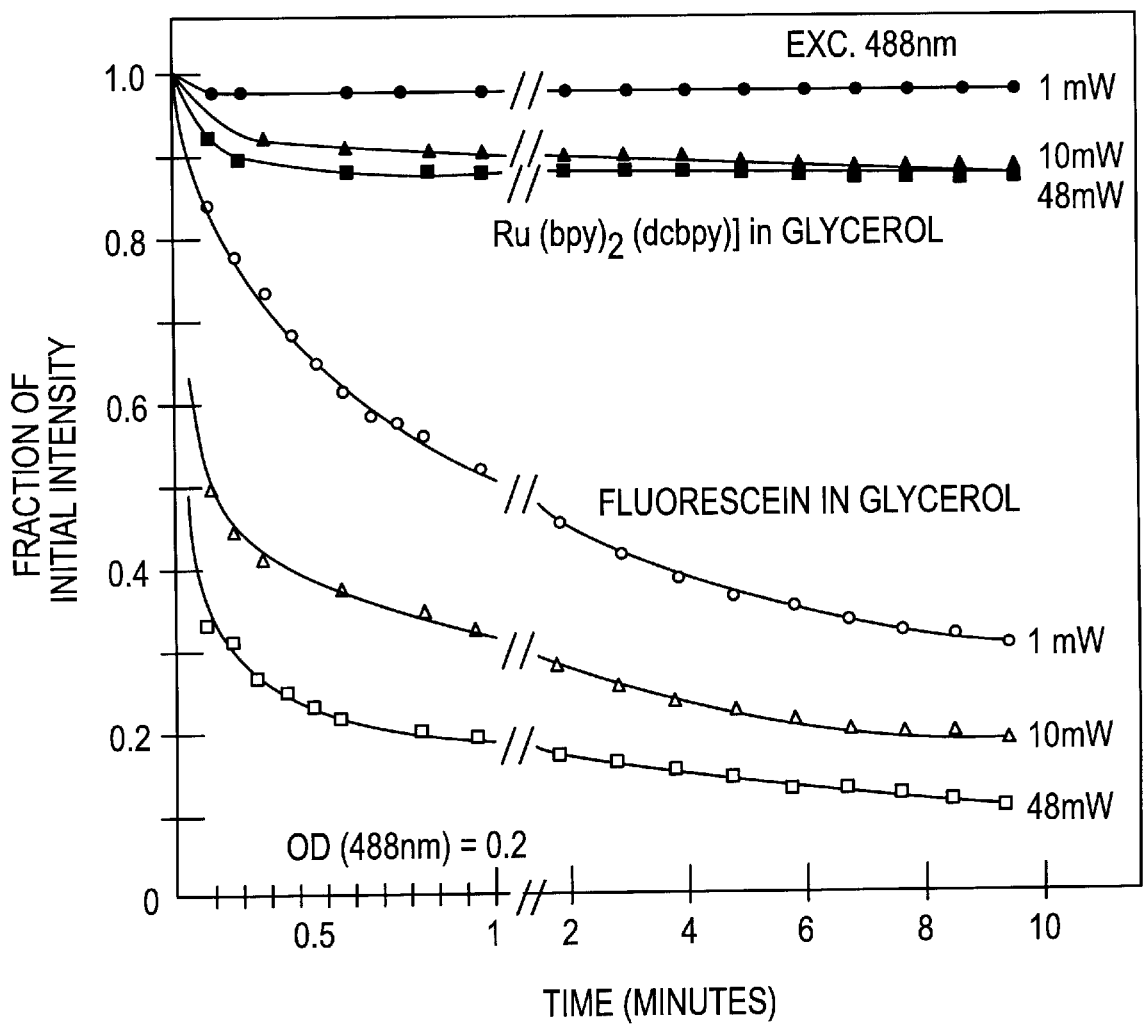
FIG. 2 graphically shows the high photochemical stability of the metal-ligand complexes.
Figure 3A:
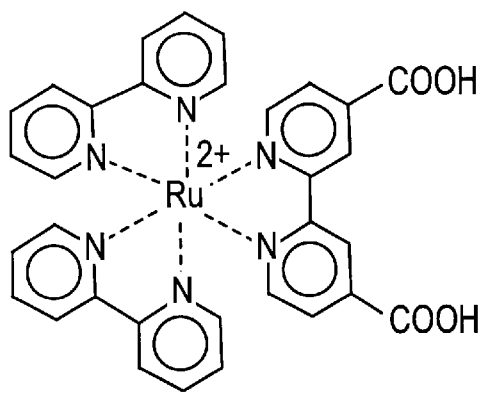
FIG. 3 graphically shows that the emission maximum of the metal-ligand complex can be altered by selection of the metal.
Figure 3B:
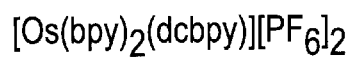
Figure 3B:
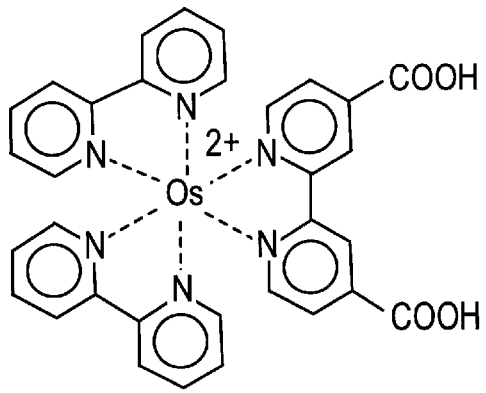
Figure 3C:
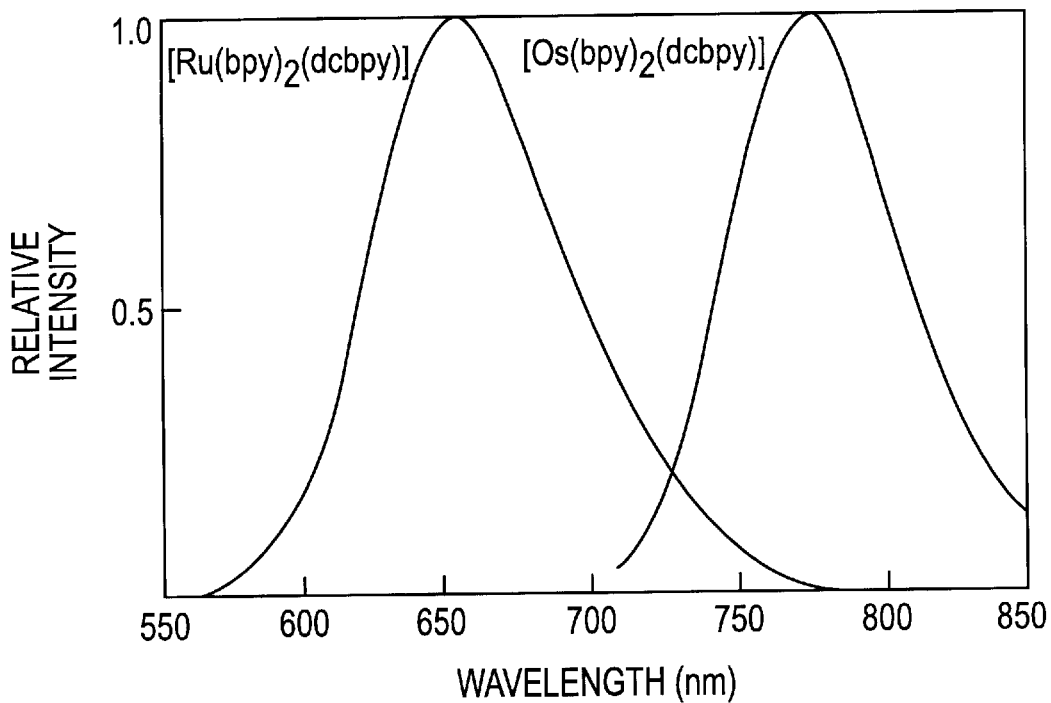
Figure 4:
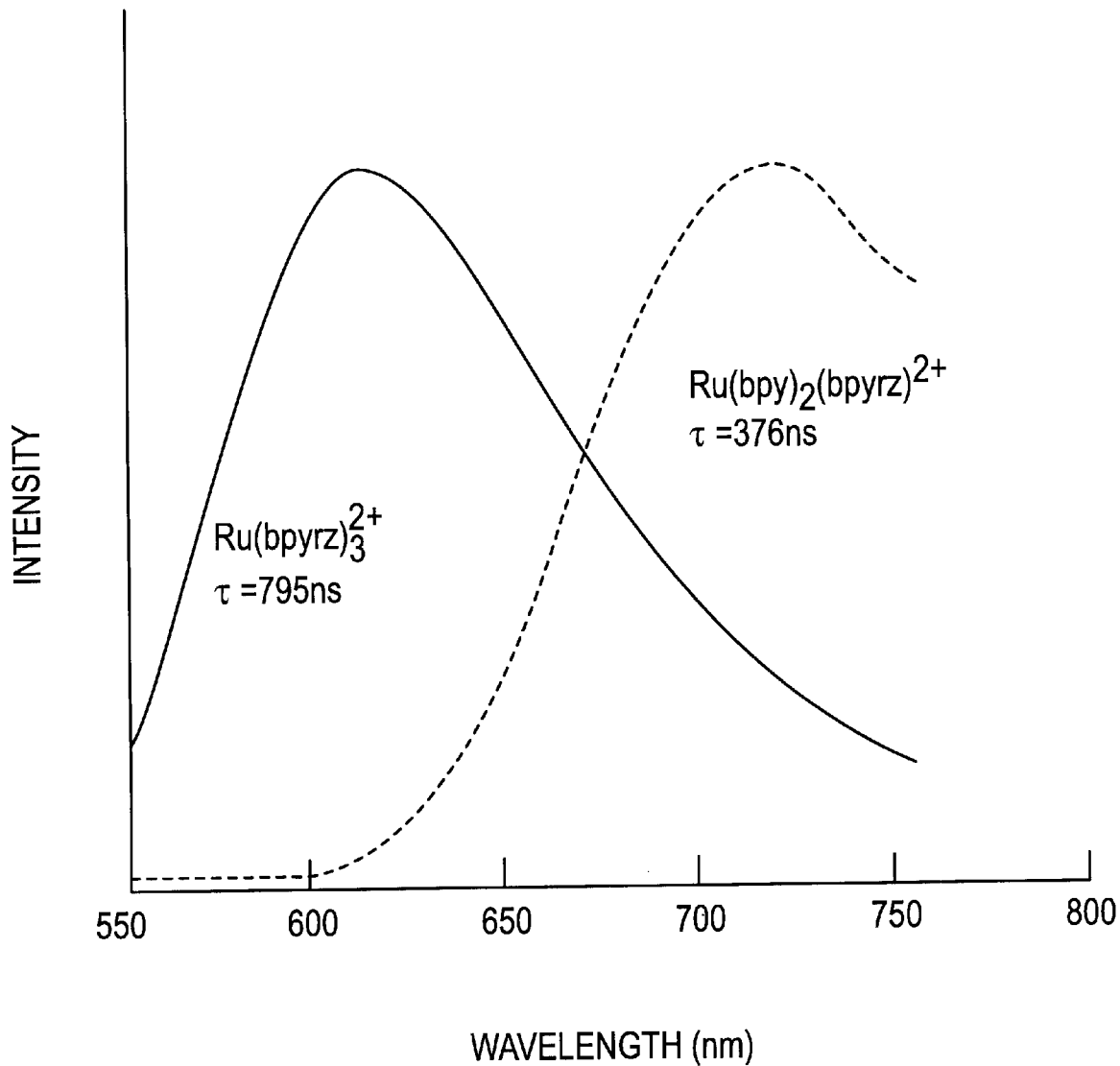
FIG. 4 graphically shows that the decay time of a metal-ligand complex can be altered by selection of the ligand.
Figure 5A:
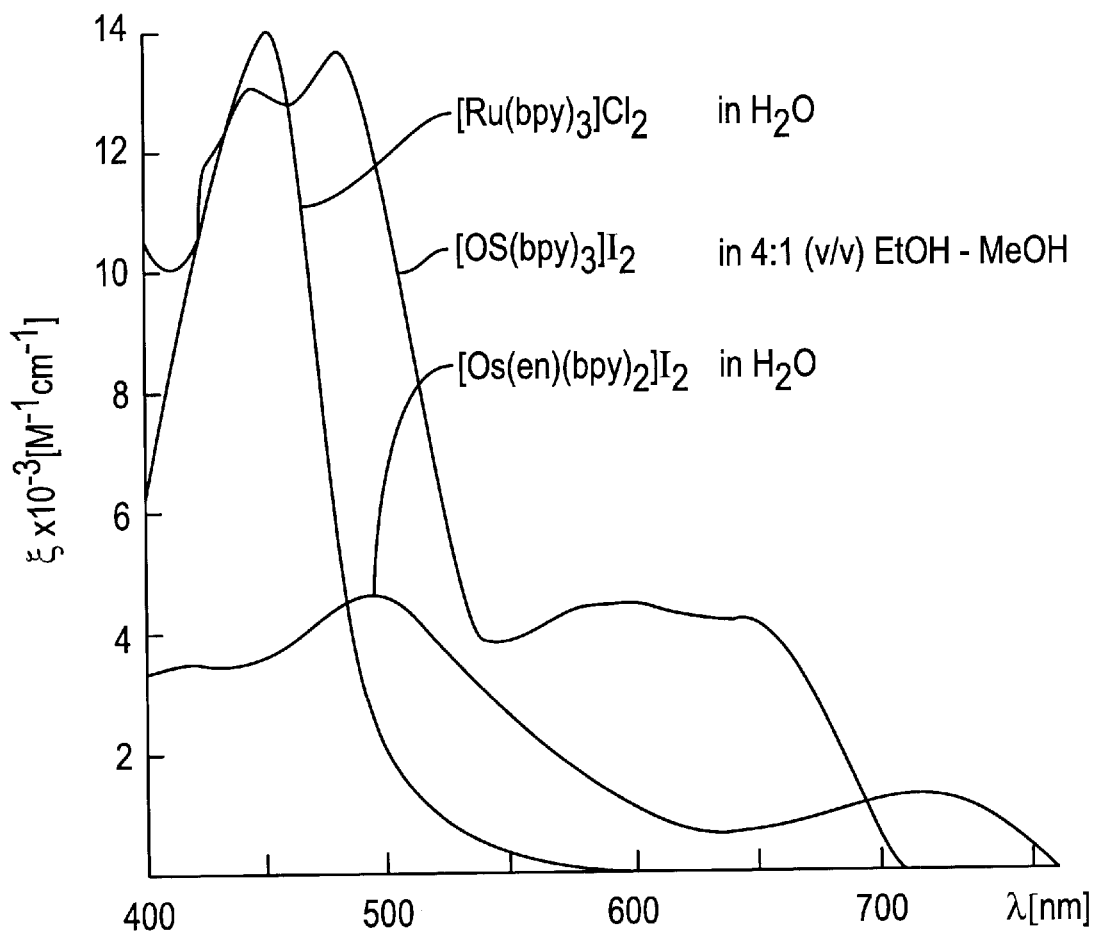
FIG. 5 graphically shows exciting metal-ligand complexes with a wide variety of simple light sources.
Figure 5B:
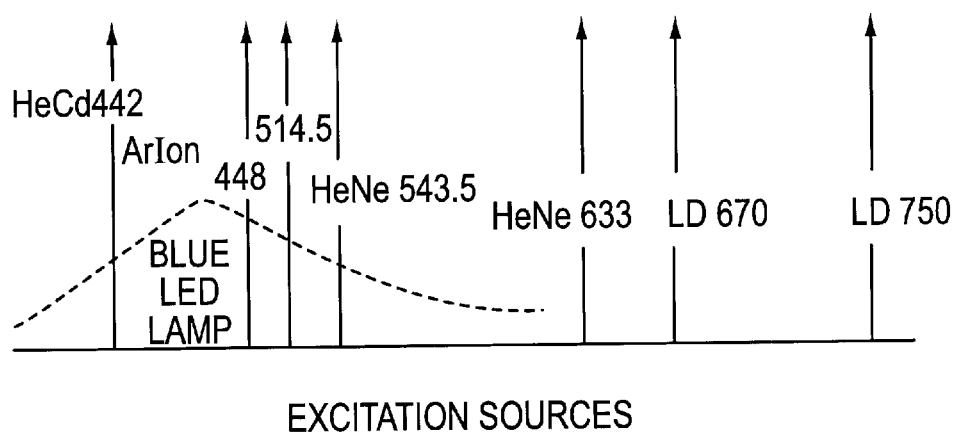
Figure 6:
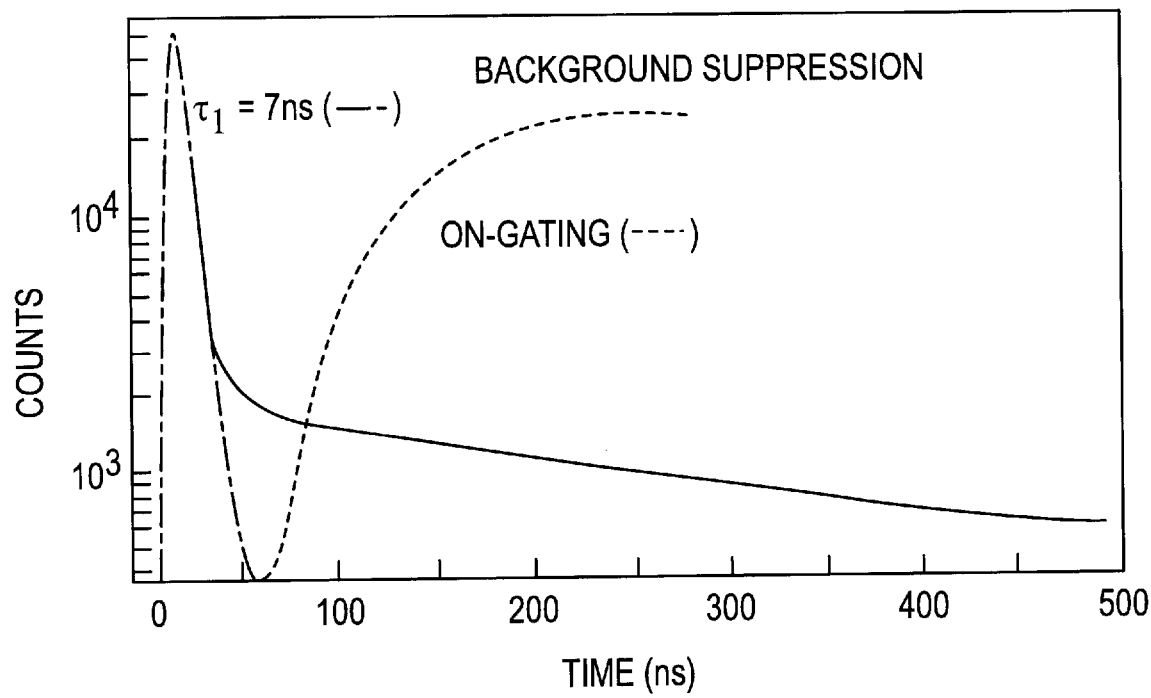
FIG. 6 is a graph depicting background suppression with a long lifetime metal-ligand complex.
Figure 7:
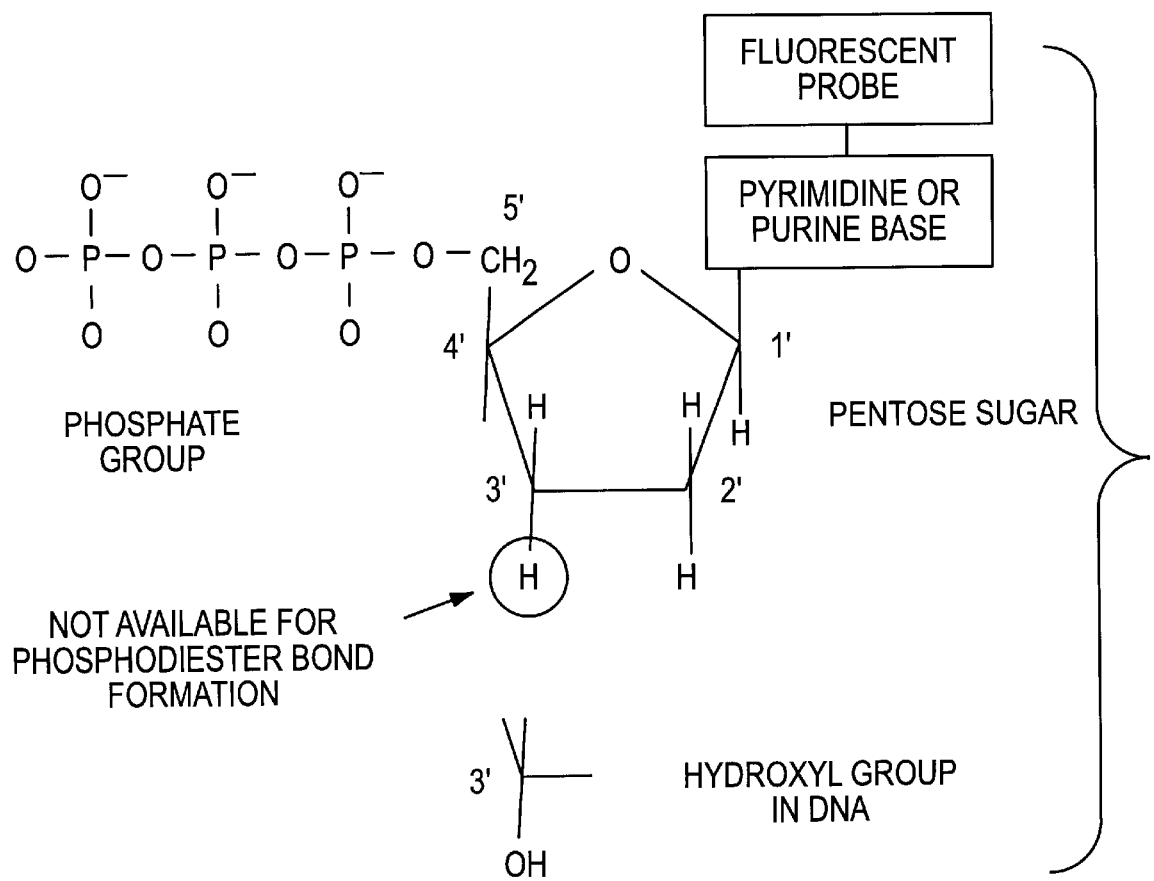
FIG. 7 graphically shows the structure of a general dideoxynucleotide triphosphate terminator which contains a fluorescent group bound to the pyrimidine or purine base. The linkage to the base is typically via amino or carbonyl groups.
Figure 8A:
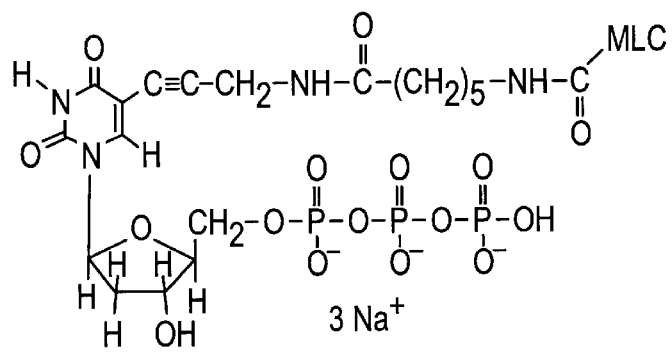
FIG. 8 graphically depicts methods to attach metal-ligand complexes to nucleotides or DNA primers. A fluorescent group can be linked via a carbon/carbon triple bond, carbon/carbon double bond, or to the phosphate of the oligonucleotide via a sulfhydryl or amino group.
Figure 8B:
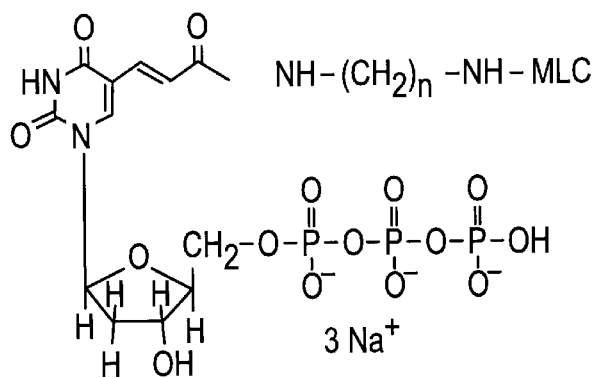
Figure 8C:
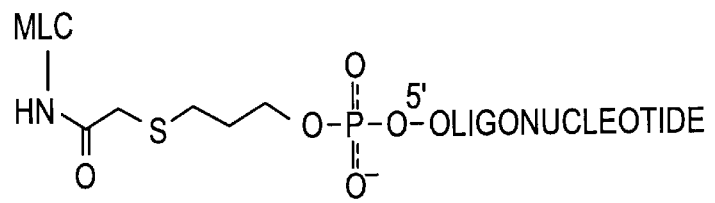
Figure 8D:
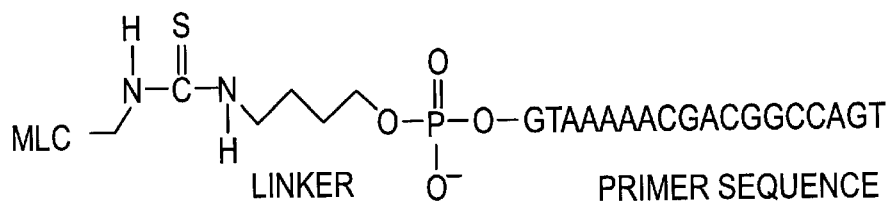
Figure 9A:
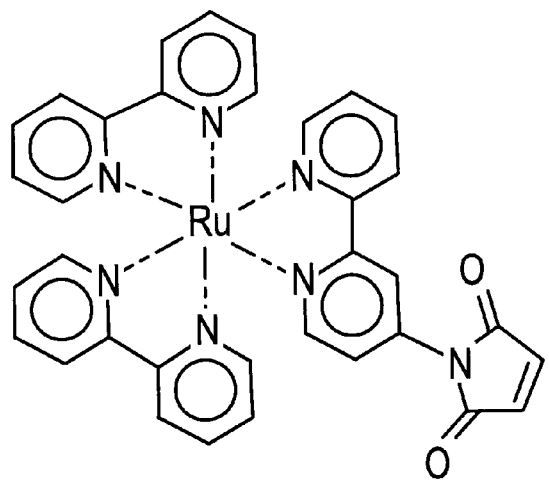
FIG. 9 shows metal-ligand complexes which are reactive with sulfhydryl or amino groups and hence can be coupled to nucleic acids.
Figure 9B:
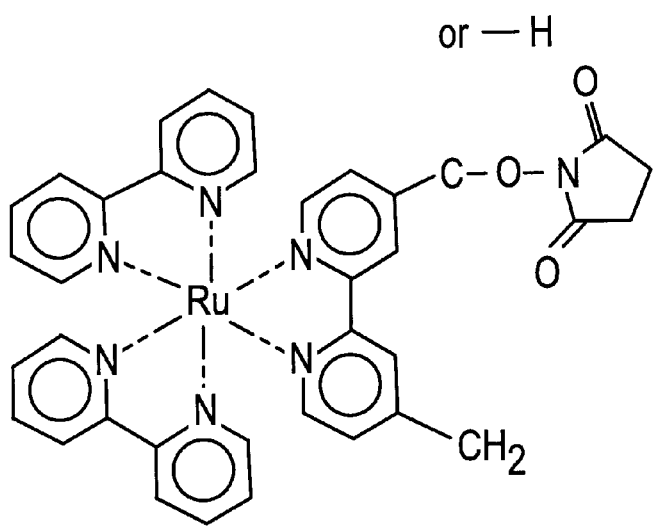
Figure 9C:
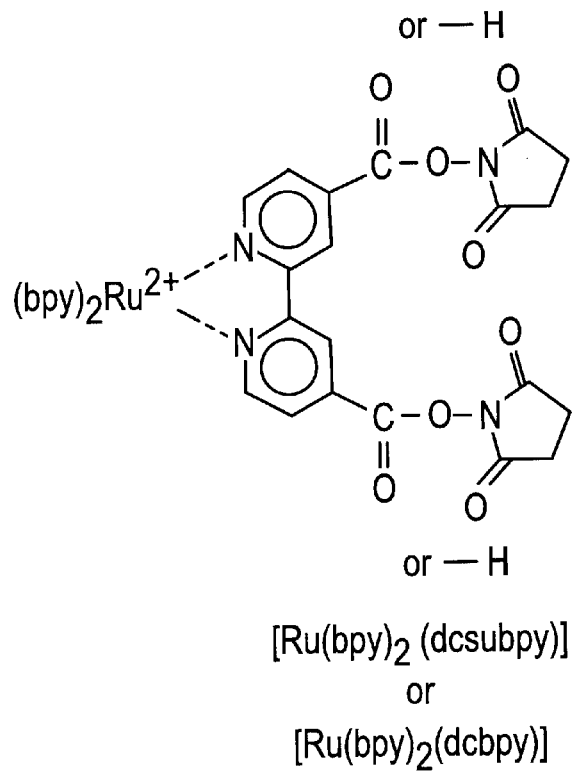
Figure 9D:
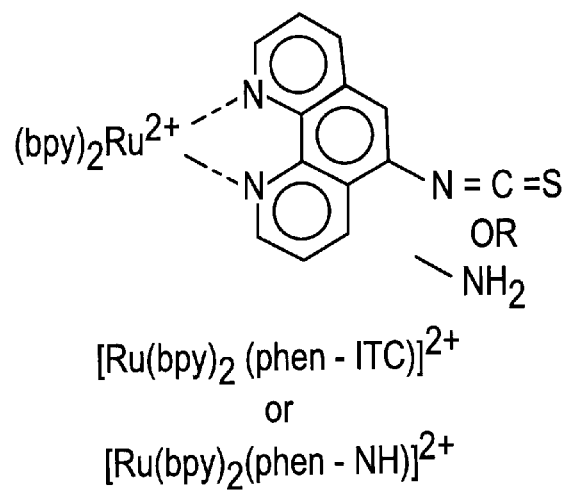
Figure 10A:
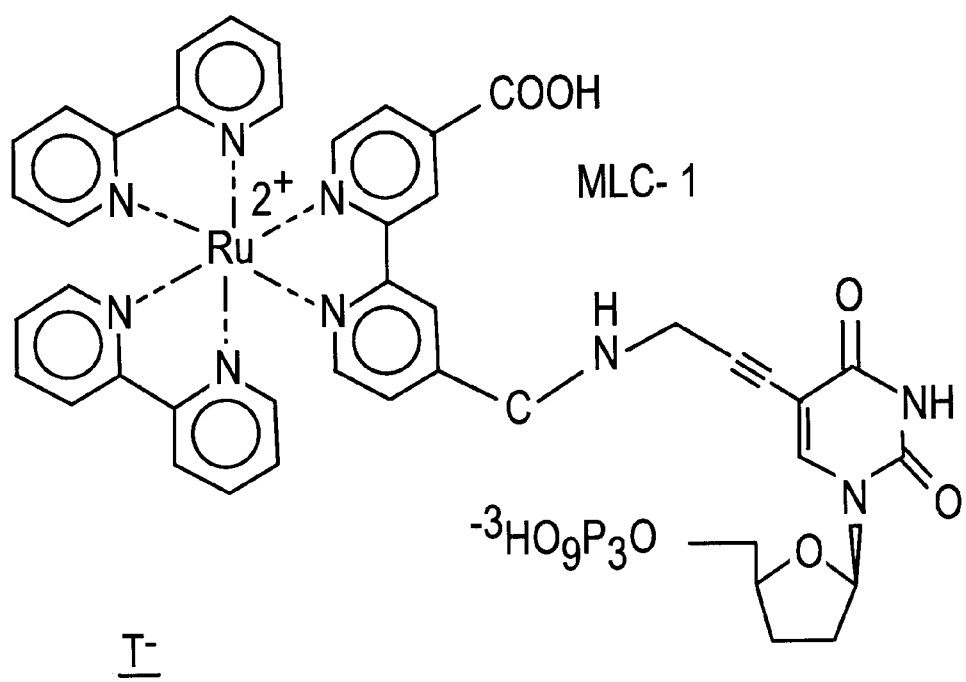
FIG. 10 shows how a set of dideoxynucleotides could be constructed based on metal-ligand complexes. One could choose four different metal-ligand complexes for sequencing based on emission spectra or lifetimes using these structures as fluorescent dideoxynucleotide triphosphate terminators.
Figure 10B:
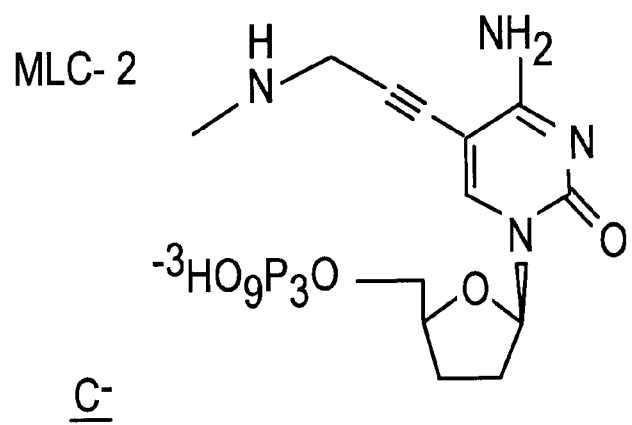
Figure 10C:
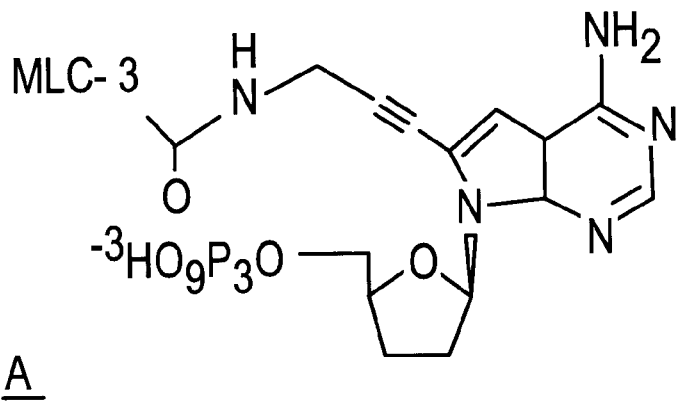
Figure 10D:
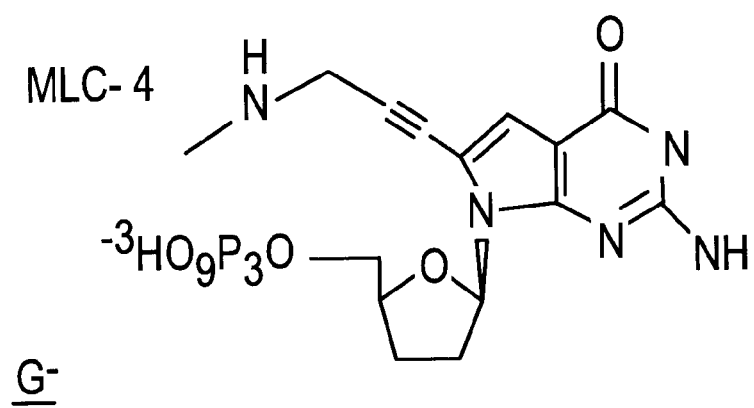
Figure 11A:
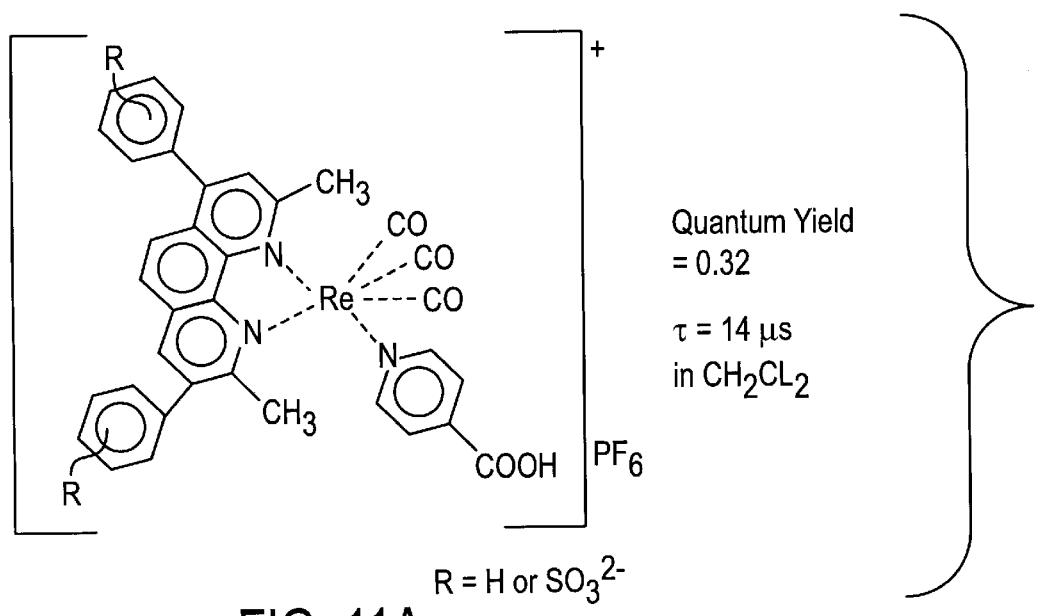
FIGS. 11 and 12 show spectral properties of other metal-ligand complexes. These figures show that one can obtain high quantum yield metal-ligand complexes for high sensitivity detection.
Figure 11B:
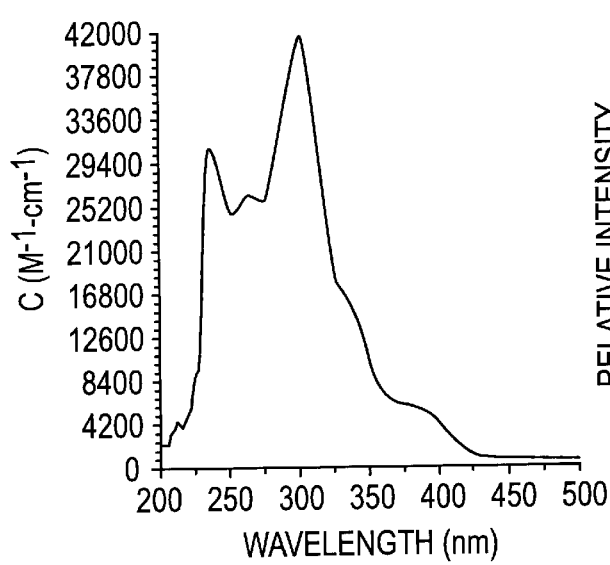
Figure 11C:
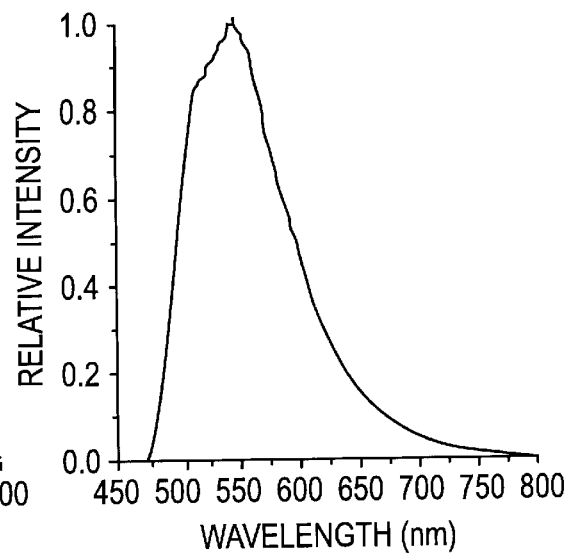
Figure 12A:
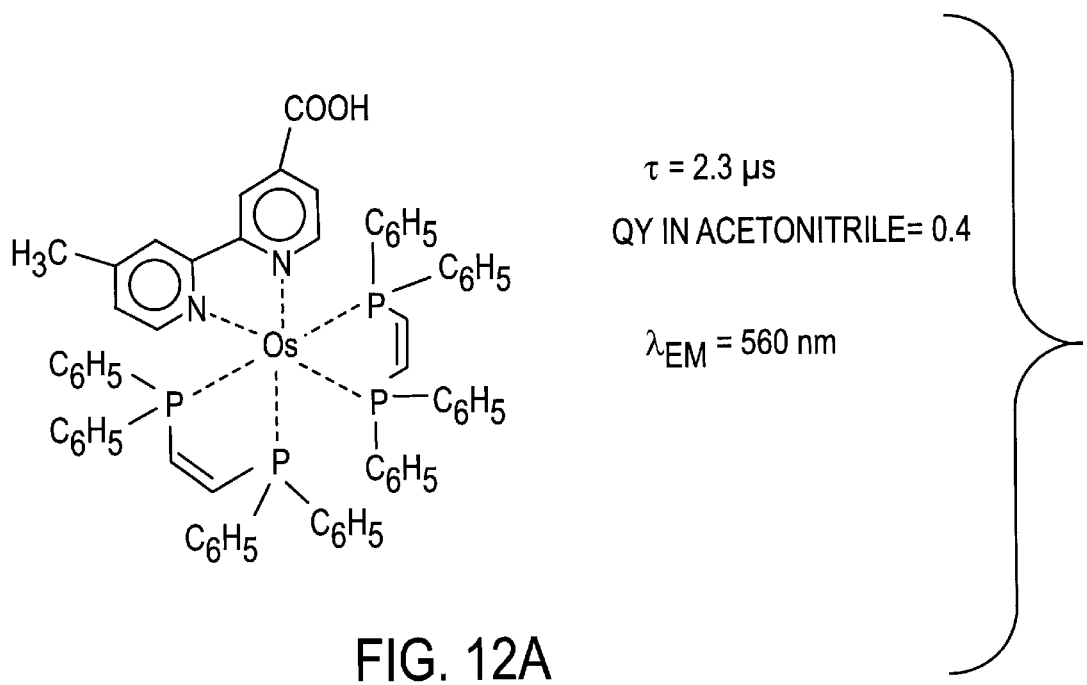
Figure 12B:
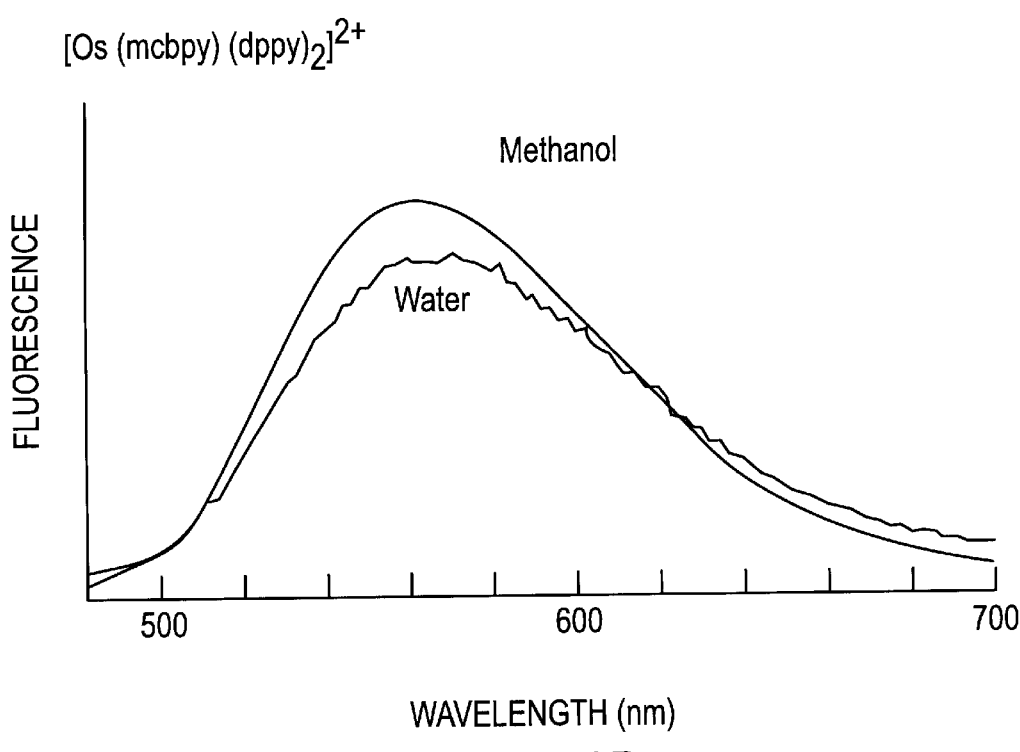
Figure 13:
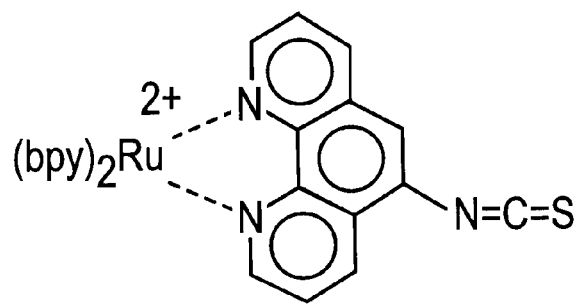
FIG. 13 is the molecular structure for [Ru(2,2'-bipyridyl)$_2$(1,10-phenanthroline-9-isothiocyanate)]$^{2+}$.
Figure 14:
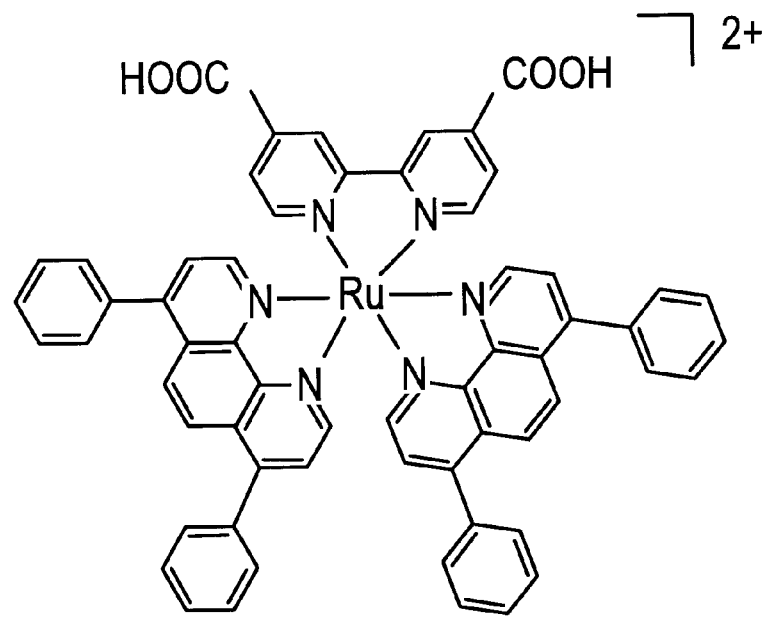
FIG. 14 is the molecular structure for [Ru(4,7-diphenyl-1,10-phenanthroline)$_2$(4,4'-dicarboxylic acid-2,2'-bipyridine)]$^{2+}$.
Figure 15:
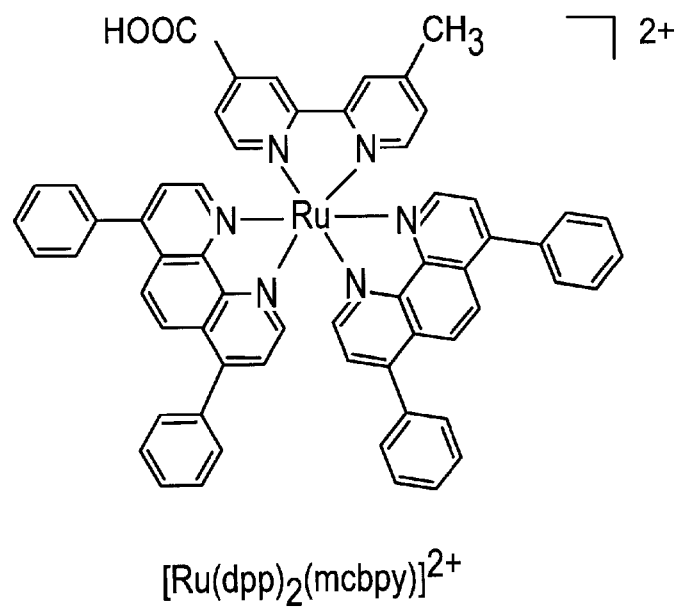
FIG. 15 is the molecular structure for [Ru(4,7-diphenyl-1,10-phenanthroline)$_2$(4-methyl,4'-carboxylic acid-2,2'-bipyridine)]$^{2+}$.
Figure 16:
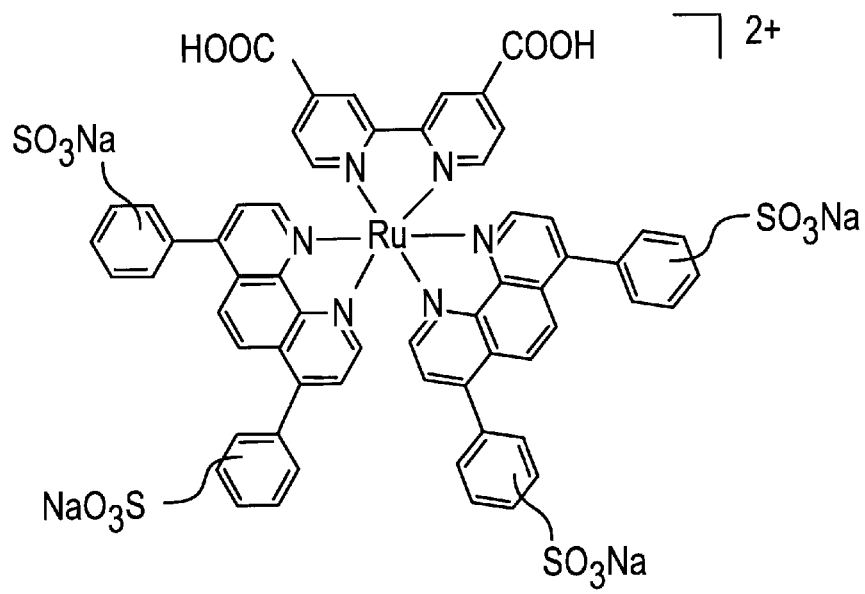
FIG. 16 is the moleclular structure for [Ru(4,7-diphenyl-1,10-phenanthroline(SO$_3$Na)$_2$)$_2$(4,4'-dicarboxylic acid-2,2'-bipyridine)]$^{2+}$.
Figure 17:
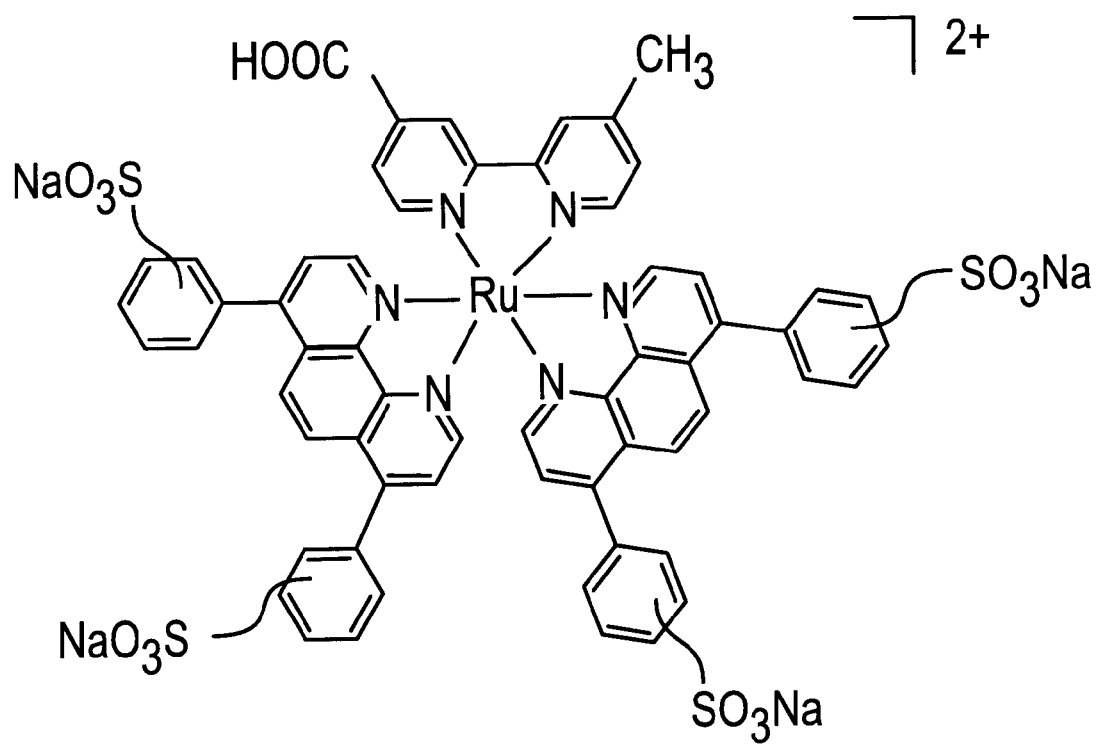
FIG. 17 is the molecular strucutre for [Ru(4,7-diphenyl-1,10-phenanthroline(SO$_3$Na)$_2$)$_2$(4-methyl, 4'-carboxylic acid-2,2'-bipyridine)]$^{2+}$.
Figure 18:
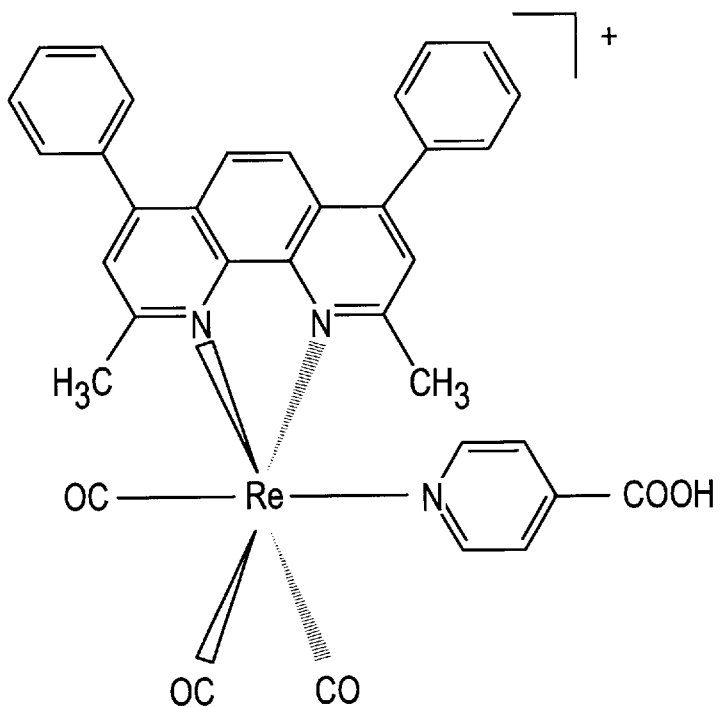
FIG. 18 is the molecular structure for [Re(2,9-dimethyl-4,7-diphenyl-1,10-phenanthroline)(CO)$_3$(isonicotinic acid)]$^+$.
Figure 19:
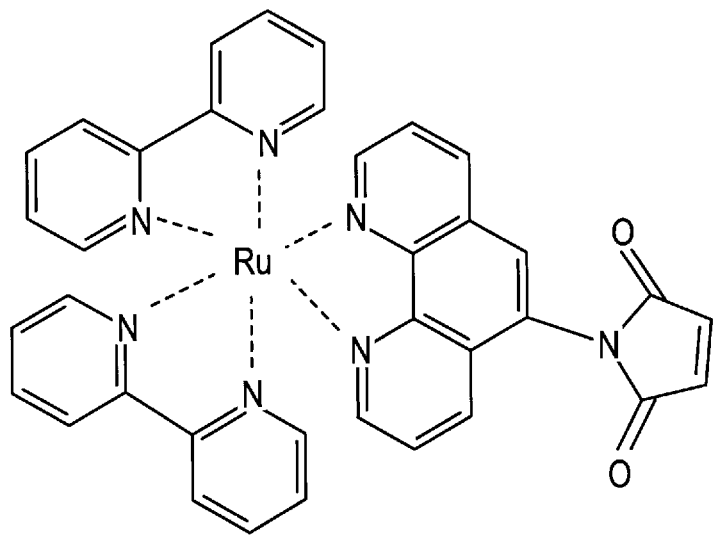
FIG. 19 is the molecular structure for [Ru bis(2,2'-bipyridyl)(phenanthroline-maleamide)].
Figure 20:
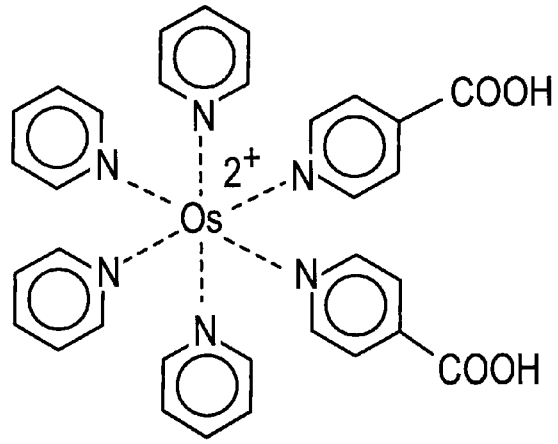
FIG. 20 is the molecular structure for (bis(2,2'-bipyridine)(4,4'-dicarboxy-2,2'-bipyridine)osmium (II) hexafluorophosphate.
Figure 21:
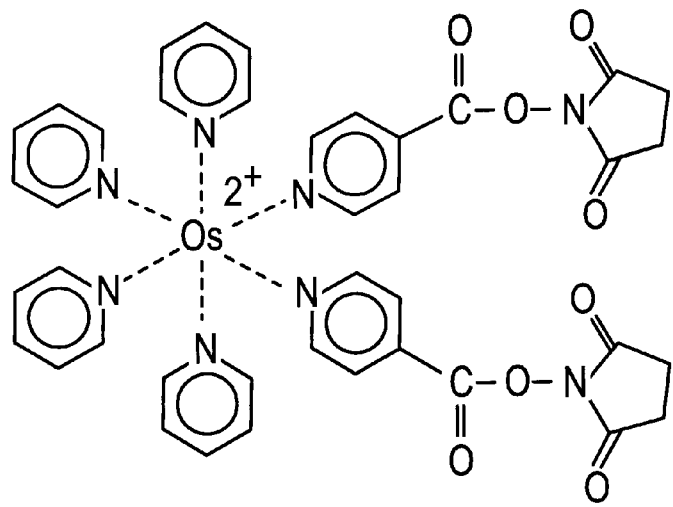
FIG. 21 is the molecular structure for bis(2,2'-bipyridine)(4,4'-succidimidyl-2,2'-bipyridine)osmium (II) hexafluorophosphate.
Figure 22:
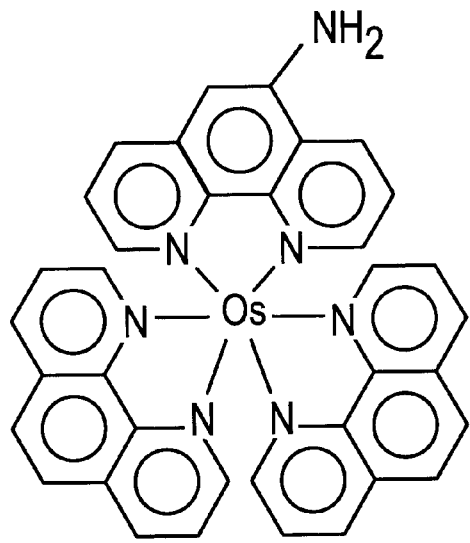
FIG. 22 is the molecular structure for bis(1,10-phenanthroline)(5-amino-1,10-phenanthroline)osmium (II).
Figure 23:
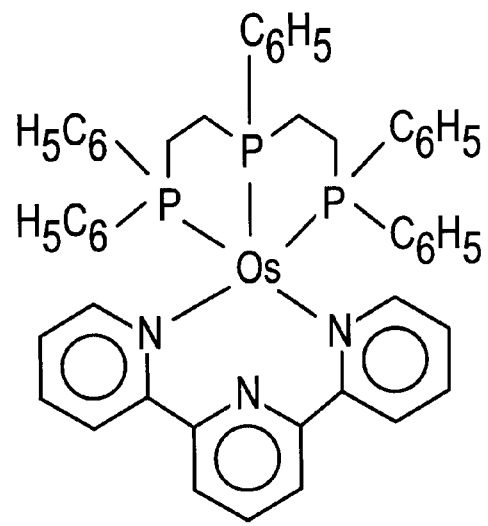
FIG. 23 is the molecular structure for (2,2',2"-terpyridine)(triphos)osmium (II).

In accordance with one embodiment of the present invention, a method is disclosed for determining a base sequence for a nucleotide strand by detecting the fluorescence of metal-ligand complexes.

In accordance with another embodiment of the present invention, a combination, which includes a fluorescent metal-ligand complex, for use in nucleotide sequencing is disclosed.

The invention utilizes fluorescent metal-ligand complexes to identify the nucleotide bases in DNA sequencing. The use of fluorescent metal-ligand complexes, as opposed to the commonly used probes attached to DNA, solves the problems of nanosecond decay times, which do not allow suppression of prompt auto-fluorescence, limited photostability, and spectral overlap between the emission spectra.

Fluorescent metal-ligand complexes have the advantage of long decay times (to 4,000 nanoseconds). The long decay times are advantageous because the detector can be gated off during pulse or modulated illumination. Such methods avoid the prompt auto-fluorescence or background fluorescence which occurs on the nanosecond time scale. The long lifetimes also allow for very simple instrumentation, so that illumination can be with laser diodes, LEDs, electroluminescent devices, and flash lamps.

Another advantage of metal-ligand complexes is their photostability, which will allow illumination with moderately intense light sources and collection of data for moderate periods of time to improve signals to noise levels.

A further advantage of this invention is the use of fluorescent metal-ligand complex probes which display different emission wavelengths or decay times for each nucleotide. Fluorescent metal-ligand complexes can be identified displaying emission spectra ranging from 350 nanometers to over 1,000 nanometers. Fluorescent metal-ligand complexes can also be identified with decay times ranging from 10 nanoseconds to 10 microseconds, allowing identification of the DNA bases from the decay times.

There are a number of metal-ligand complexes which display luminescence, including complexes containing Co, Cr, Cu, Mo, Ru, Rh, W, Re, Os, Ir, or Pt. In particular, transition metal complexes, especially those with Ru, Os, Re, Rh, Ir, W or Pt, can be used. The metal in the metal-ligand complex is particularly preferably selected from the group consisting of ruthenium, osmium, and rhenium.

A suitable ligand in the metal-ligand complex can be polypyridine, bipyridine, or a related compound, and the ligand can contain a reactive group commonly used for linkage to biological molecules, such as a N-hydroxysuccinimide ester of a carboxylic acid, haloacetyl groups, maleimides, sulfonyl chlorides, and isothiocyanates. Other ligands for such metal-ligand complexes are bipyrazyl, phenanthroline, and related substituted derivatives, or inorganic ligands such as CO, Cl, nitrile and isonitrile.

Preferred metal-ligand complexes include [Ru(2,2'-bipyridyl)$_2$(1,10-phenanthroline-9-isothiocyanate)]$^{2+}$, [Ru(4,7-diphenyl-1,10-phenanthroline)$_2$(4,4'-dicarboxylic acid-2,2'-bipyridine)]$^{2+}$, [Ru(4,7-diphenyl-1,10-phenanthroline)$_2$(4-methyl,4'-carboxylic acid-2,2'-bipyridine)]$^{2+}$, [Ru(4,7-diphenyl-1,10-phenanthroline(SO$_3$Na)$_2$)$_2$(4,4'-dicarboxylic acid-2,2'-bipyridine)]$^{2+}$, [Ru(4,7-diphenyl-1,10-phenanthroline(SO$_3$Na)$_2$)$_2$(4-methyl,4'-carboxylic acid-2,2'-bipyridine)]$^{2+}$, [Re(2,9-dimethyl-4,7-diphenyl-1,10-phenanthroline)(CO)$_3$(isonicotinic acid)]$^+$, [Ru bis(2,2'-bipyridyl)(phenanthroline-maleamide)], (bis(2,2'-bipyridine)(4,4'-dicarboxy-2,2'-bipyridine)osmium (II) hexafluorophosphate, bis(2,2'-bipyridine)(4,4'-succidimidyl-2,2'-bipyridine)osmium (II) hexafluorophosphate, bis(1,10-phenanthroline)(5-amino-1,10-phenanthroline)osmium (II), and (2,2',2"-terpyridine)(triphos)osmium (II).

Metal-ligand complexes have not been applied to the widely practiced field of DNA sequencing. These complexes provide substantial technological advantages and are widely adaptable for use in place of known fluorophores in any suitable DNA sequencing method.

DNA sequencing first became practical in 1977. The original method involved selective chemical degradation of the DNA, followed by chromatography and detection of the fragments by $^{32}$P autoradiography. In the same year an improved method based on chain-terminating dideoxynucleotides and $^{32}$P also became available. An overview of the history of DNA sequencing methods can be found in the informative text by Watson et al.

In DNA the nucleotides are linked in a continuous strand via the 5' and 3' hydroxyl groups of the pentose sugar. DNA is replicated by adding bases to the 3' hydroxyl group. This elongation reaction is catalyzed on the unknown sequence by DNA polymerase, starting at a primer location of known sequence. The absence of a 3' hydroxyl group on the ddNTPs prevents further elongation and termination of the reaction. The DNA polymerase reaction is terminated along the sequence by the ddNTPs which are randomly added along the growing chain. This results in a variety of oligonucleotides of varying length, which are separated by polyacrylamide gel electrophoresis. Remarkably, all the fragments differing by just one base pair can be resolved, up to several hundred bases. Typically there are four different terminating nucleotides, and each reaction mixture is electrophoresed in a separate lane. The gels separate the DNA fragments according to size, so that the sequence can be determined from the autoradiogram of the separated DNA fragments.

The use of the dideoxyoligoncleotide terminators is now the preferred sequencing method, but with the use of fluorescence in place of $^{32}$P. The use of radioactive tracers is obviously problematic with regards to cost, safety and disposal. DNA sequencing using fluorescence first became possible in 1986. Several methods were proposed, the first based on the use of four different fluorescent primers and non-fluorescent dideoxynucleotides, and another based on the use of four different fluorescent dideoxynucleotides. DNA sequencing can also be accomplished with a single fluorescent primer and non-fluorescent ddNTPs. Either the primers or the ddNTPs can be fluorescent. If the fluorophores are all distinct, then the DNA can be electrophoresed in a single line and the bases identified by the emission spectra. One can also use a single fluorescent primer, non-fluorescent ddNTPs, and perform the electrophoresis in four lanes. All these variations are in common use in DNA sequencing.

A description of methods for synthesizing the reactive oligonucleotides is disclosed in Smith, L. M., Kaiser, R. J., Sanders, J. Z., and Hood, L. E., "The Synthesis and Use of Fluorescent Oligonucleotides in DNA Sequencing Analysis," *Methods in Enzymology* 155:260–301 (1987).

A variety of fluorophores have been chosen for DNA sequencing, typically a set of four fluorophores, one for each base A, C, G or T. The fluorophores are typically selected so that all can be excited using the 488 nm line from an argon ion laser. While all four dyes could be excited at 488 nm, absorption of Texas Red and tetramethylrhodamine is weak at 488 nm. For this reason it is necessary to use excitation at 514 nm to obtain relatively equal intensities of all four probes. Another difficulty with these four dyes is the overlapping emission spectra. For this reason it is necessary to record the emission spectra of the gels at more than one excitation and emission wavelength. In spite of these difficulties the use of four fluorophores allowed using a single gel column containing the mixture of labeled DNA fragments.

In the previous paragraphs we mentioned some of the non-ideal properties of the dyes. These considerations illustrated what features are important in dyes for DNA sequencing. Useful dyes can be excited with a convenient laser source, and will provide similar intensities for excitation at a single wavelength. The use of fluorescence has allowed DNA sequencing to become routine in numerous laboratories. Capillary gel electrophoresis is being used in place of slab gels, providing more rapid separations with increased resolution. Some capillary columns have been described as yielding 1000 bases per hour. Other groups have described instruments with up to 100 capillary columns. Hence it seems clear that sequencing technology is poised for further improvements.

A wide variety of chemical structures have been used to covalently label DNA. One typical linkage is an acetylene linkage to the bases. Probes can be attached to the 5' end of DNA via a sulfhydryl group linked to the terminal phosphate. Amino groups can also be placed on the terminal phosphate. Alternatively, fluorophores have been linked to the bases themselves, typically opposite to the base recognition hydrogen binding side of the base. The 5' phosphate can be made reactive with iodoacetamide probes by attaching a terminal —$PO_3S$ residue.

For DNA sequencing it is desirable to have dyes which display distinct emission spectra and similar intensities with a single excitation wavelength. This is difficult to accomplish using a single fluorophore. Hence, donor-acceptor pairs have been used to accomplish these requirements. The emission spectra of such probes are moderately distinct, suggesting they would allow sequencing in a single lane. However, the intensities were found to be rather unequal when excited at a single wavelength of 488 nm. For this reason the donors and acceptors were covalently linked within the Forster distance ($R_0$) using reactive oligonucleotides or DNA-like sugar polymers without the nucleotide bases.

Energy transfer is useful in equalizing intensities. The probes show similar absorbance at 488 nm, and the emission intensities are relatively equal. These probes show emission spectra which are moderately well separated, which is easier to see in the normalized emission spectra. The bases can be readily identified by measurement at the emission wavelengths, and allow DNA sequencing with capillary electrophoresis using a single 488 nm excitation wavelength. However, the emission spectra overlap and there is residual emission from the donors which contributes to the intensities at shorter wavelengths. Hence, there is still a need for improved dyes for DNA sequencing.

A description of energy transfer primers for DNA sequencing is disclosed in Ju, J., Ruan, C., Fuller, C. W., Glazer, A. N., and Mathies, R. A., "Fluorescence energy transfer dye labeling primers for DNA sequencing and analysis," *Proc. Natl. Acad. Sci. USA* 92:4347–51 (1995). The possibility of using energy transfer primers for energy transfer probes allows one to obtain similar intensities at a single excitation wavelength. In the case of the metal-ligand complexes, there is the additional advantage of the higher extinction coefficient of most organic chromophores compared with the metal-ligand complexes. Hence, sensitivity might be enhanced by using energy transfer from a high extinction coefficient dye to a long lifetime metal-ligand complex.

To satisfy the demands of the human genome project it is necessary to sequence DNA as inexpensively as possible. One means of decreasing the cost is to use semiconductor laser diodes, which are now available from 630 nm to longer wavelengths. These lasers consume little power and can operate for up to 100,000 hours between failures. An additional advantage of red and NIR excitation is the lower autofluorescence from biological samples, gels, solvents and optical components.

It is difficult to obtain four dyes with similar absorption spectra and different emission spectra. Such dyes would allow determination of all four bases on a single gel column; which is highly desirable for more rapid sequencing. The use of decay times, instead of emission maxima, offers an alternative method to identify the bases. An additional advantage of lifetime-based sequencing is that the decay times are mostly independent of intensity. If decay times are used to identify the bases, the emission spectra can overlap, possibly making it easier to identify suitable fluorophores. Several groups have made progress towards lifetime-based sequencing. The decay times for the initially proposed DNA sequencing dyes have been measured in polyacrylamide gels under sequencing conditions. While the decay times are different for each dye, pulsed light sources at 488 and 514 nm are not practical for sequencing. The source would need to be an argon ion laser, which was pulsed or modulated by some internal (mode-locker) or external means (modulator).

A set of lifetime DNA dyes excitable at 636 nm has been proposed. The decay times are seen to range from 3.6 to 0.7 ns. However, some of these dyes are quenched when bound to oligonucleotides. Nonetheless, the greater ease of obtaining different lifetimes suggests continued research and progress in lifetime-based sequencing.

One embodiment of the present invention utilizes osmium-ligand complexes, which display lifetimes ranging from 50 nanoseconds to 3,600 nanoseconds. These compounds are known to be highly stable.

Another embodiment of the present invention utilizes selection of complexes with different lifetimes, so that the terminal nucleotides can be identified by the decay time of the label. Lifetime measurements are presently possible by measurements using either the time domain or the frequency domain, but the instrumentation is complex for nanosecond decay times. Alternately, fluorescence lifetime imaging of the gels which contain the labeled DNA can be utilized.

A description of the lifetime imaging apparatus is provided in U.S. Pat. No. 5,485,530.

In another embodiment of the invention, capillary electrophoresis is used to determine the base sequence. Descriptions of the prior capillary electrophoresis methods are disclosed in the following references:

X. C. Huang, M. A. Quesada, and R. A. Mathies, "DNA Sequencing Using Capillary Array Electrophoresis," *Anal. Chem.*, 64, 2149–2154 (1992).

S. A. Soper, B. L. Legendre, Jr., and D. C. Williams, "On-Line Fluorescence Lifetime Determinations in Capillary Electrophoresis," *Anal. Chem.*, 67, 4358–4365 (1995).

B. L. Legendre, Jr., D. C. Williams, and S. A. Soper, "An All Solid-State Near-Infrared Time-Correlated Single Photon Counting Instrument For Dynamic Lifetime Measurements in DNA Sequencing Applications," *Rev. Sci. Instrum.*, 67(11), 3984–3989 (1996).

K. Ueno and E. S. Yeung, "Simultaneous Monitoring of DNA Fragments Separated By Electrophoresis in a Multiplexed Array of 100 Capillaries," *Anal. Chem.*, 66, 1424–1431 (1994).

DNA chip technology, which utilizes light directed matrices, may be used in another embodiment of the present invention. This technology is available in Affymetrix's GeneChip and Hyseq's SuperChips.

The steps of the invention may be repeated to sequentially identify further bases of the nucleotide strand, until the strand is completely sequenced.

The invention is further illustrated by the following examples, which are not intended to be limiting.

EXAMPLE 1

The M13/pUC forward sequencing primer (5'-CCCAGTCACGACGTTGTAAAACG-3') (SEQ ID NO:1) is amino-modified at the 5' end by first adding an ATP with T4 polynucleotide kinase and then reacting it with carbodiimide at pH 6. This amine-containing oligonucleotide (about 50 nmol) is dissolved in in 1 mL of 0.2 M bicarbonate buffer, pH 9. A fluorescent amine-reactive metal ligand complex is dissolved in DMF (10 mg/mL), out of which 50 μL is added to the amino-oligonucleotide. The reaction is allowed to proceed overnight at room termpature. The labeled oligonucleotide is separated from the free dye by passing it throught Sephadex G-25. Further purification may be done by RP-HPLC.

Annealing of the labeled primer to the DNA template is accomplished by mixing a 1:1 molar ratio of primer to DNA in Tris buffer, pH 7.5, and heating the mixture to 65° C., then cooling it slowly to room temperature. DNA polymerase is added to the solution and then the mixture is divided into four equal parts in tubes labeled A, T, C, and G. To the tube labeled A, a mixture of dTTP, dCTP, dGTP, and dideoxy-ATP (ddATP) is added. To the tube labeled, T, a mixture of dATP, dCTP, dGTP, and ddTTP is added. To the tube labeled C, a mixture of dATP, dTTP, dGTP, and ddCTP is added. To the tube labeled G, a mixture of dATP, dTTP, dCTP, and ddGTP is added. The mixtures are incubated at 37° C. for about 5 minutes. The reactions are stopped by adding a solution of formamide/EDTA. The DNA is precipitated with sodium acetate and ethanol, dried, and resuspended in formamide/EDTA. The DNA is denatured by heating the solution to 95° C. for 1 minute and then it is loaded onto a denaturing polyacrylamide gel or a capillary gel electrophoresis apparatus.

EXAMPLE 2

A second, third, and fourth amine-reactive metal ligand complex are reacted with the M13/pUC sequencing primer as in Example 1. The four metal ligand complexes differ in fluorescence lifetime and emission maxima, but are designed to have substantially the same electrophoretic mobility. A different metal ligand complex labeled primer is mixed with each termination mix after which the reaction mixtures are combined into one vial. The DNA is precipitated, resuspended in buffer, and treated as in Example 1.

Since many modifications, variations, and changes in detail may be made to the described embodiments, it is intended that all matter in the foregoing description and shown in the accompanying drawings be interpreted as illustrative and not in a limiting sense.

---

---

What is claimed is:

1. A method for determining a base sequence of a nucleotide strand comprising the steps of:

(a) providing a first probe, comprising a fluorescent metal-ligand complex coupled to a first oligonucleotide having a sequence complementary to a first fragment of said strand;

(b) adding said first probe to a sample that contains said first fragment to form a first mixture containing a first reaction product of said first probe and said first fragment;

(c) exposing said first mixture to an exciting amount of radiation;

(d) detecting fluorescence of said first metal-ligand complex;

(e) identifying a first base sequence of said first fragment based on fluorescence of said first metal-ligand complex;

(f) providing a second probe, comprising a second fluorescent metal-ligand complex coupled to a second oligonucleotide having a sequence complimentary to a second fragment of said strand differing from said first fragment by at least one base;

(g) adding said second probe to a sample that contains said second fragment to form a second mixture containing a second reaction product of said second probe and said second fragment;

(h) exposing said second mixture to an exciting amount of radiation;

(i) detecting fluorescence of said second metal-ligand complex;

(j) identifying a second base sequence of said second fragment based on fluorescence of said second metal-ligand complex;

(k) comparing said second base sequence with said first base sequence to identify a difference between the first and second sequences and thereby determine a base sequence of said nucleotide strand;

wherein the metal in each said fluorescent metal-ligand complex is selected from the group consisting of Co, Cr, Cu, Mo, Rh, W, Re, Os, Ir, and Pt;

wherein said detection utilizes measurement of fluorescence lifetime; and wherein autofluorescence is suppressed by fluorescence gating.

2. A method as defined by claim 1, wherein steps (f) through (k) are repeated to sequentially identify further bases of said nucleotide strand.

3. A method as defined by claim 1, wherein the metal in each said fluorescent metal-ligand complex is Os.

4. A method as defined by claim 1, wherein said exciting amount of radiation is at a wavelength of about 450 nm.

5. A combination for use in nucleotide sequencing:

(a) a first probe comprising a fluorescent metal-ligand complex coupled to a first oligonucleotide having a sequence complementary to a first fragment of a nucleotide strand; and (b) a second probe comprising a fluorescent metal-ligand complex coupled to a second oligonucleotide having a sequence complementary to a second fragment of said nucleotide strand differing from said first fragment by at least one base;

wherein the metal in each said fluorescent metal-ligand complex is selected from the group consisting of Co, Cr, Cu, Mo, Rh, W, Re, Os, Ir, and Pt.

6. A combination as defined by claim 5, wherein the metal in each said fluorescent metal-ligand complex is Os.

7. A method for determining a base sequence of a nucleotide strand comprising the steps of:

(a) providing a first probe, comprising a fluorescent metal-ligand complex coupled to a first oligonucleotide having a sequence complementary to a first fragment of said strand;

(b) adding said first probe to a sample that contains said first fragment to form a first mixture containing a first reaction product of said first probe and said first fragment;

(c) exposing said first mixture to an exciting amount of radiation;

(d) detecting fluorescence of said first metal-ligand complex;

(e) identifying a first base sequence of said first fragment based on fluorescence of said first metal-ligand complex;

(f) providing a second probe, comprising a second fluorescent metal-ligand complex coupled to a second oligonucleotide having a sequence complimentary to a second fragment of said strand differing from said first fragment by at least one base;

(g) adding said second probe to a sample that contains said second fragment to form a second mixture containing a second reaction product of said second probe and said second fragment;

(h) exposing said second mixture to an exciting amount of radiation;

(i) detecting fluorescence of said second metal-ligand complex;

(j) identifying a second base sequence of said second fragment based on fluorescence of said second metal-ligand complex;

(k) comparing said second base sequence with said first base sequence to identify a difference between the first and second sequences and thereby determine a base sequence of said nucleotide strand;

wherein said fluorescent metal-ligand complex is selected from the group consisting of [Re(2,9-dimethyl-4,7-diphenyl-1,10-phenanthroline)(CO)$_3$(isonicotinic acid) ]$^+$, Bis(2,2'-bipyridine)(4,4'-dicarboxy-2,2'-bipyridine)osmium (II) hexafluorophosphate, Bis(2,2'-bipyridine)(4,4'-succidimidyl-2,2'-bipyridine)osmium (II) hexafluorophosphate, Bis(1,10-phenanthroline)(5-amino-1,10-phenanthroline)osmium (II), and (2,2',2"-terpyridine)(triphos)osmium (II);

wherein said detection utilizes measurement of fluorescence lifetime; and wherein autofluorescence is suppressed by fluorescence gating.

8. A combination for use in nucleotide sequencing:

(a) a first probe comprising a fluorescent metal-ligand complex coupled to a first oligonucleotide having a sequence complementary to a first fragment of a nucleotide strand; and (b) a second probe comprising a fluorescent metal-ligand complex coupled to a second oligonucleotide having a sequence complementary to a second fragment of said nucleotide strand differing from said first fragment by at least one base;

wherein said fluorescent metal-ligand complex is selected from the group consisting of [Re(2,9-dimethyl-4,7-diphenyl-1,10-phenanthroline)(CO)$_3$(isonicotinic acid)]$^+$, Bis(2,2'-bipyridine)(4,4'-dicarboxy-2,2'-bipyridine)osmium (II) hexafluorophosphate, Bis(2,2'-bipyridine)(4,4'-succidimidyl-2,2'-bipyridine)osmium (II) hexafluorophosphate, Bis(1,10-phenanthroline)(5-amino-1,10-phenanthroline)osmium (II), and (2,2',2"-terpyridine)(triphos)osmium (II).

9. A method as defined in claim 1, wherein said method is a primer type method.

10. A method as defined in claim 8, wherein said method is a primer type method.

11. In a method for determining the nucleotide base sequence of a nucleic acid molecule, which comprises the steps of:

a) annealing said nucleic acid molecule with a primer molecule able to hybridize to said nucleic acid molecule;

b) incubating the annealed mixture with four different deoxynucleoside triphosphates, a polymerase, and a nucleic acid synthesis terminating agent which terminates synthesis at a specific nucleotide base; and c) separating the products of step b); the improvement comprising detecting the separated products via a fluorescent metal-ligand complex, wherein when the metal in each said fluorescent metal-ligand complex is Ru, the complex is selected from the group consisting of [Ru(2,2'-bipyridyl)$_2$(1,10-phenanthroline-9-isothiocyanate)]$^{2+}$, [Ru(4,7-diphenyl-1,10-phenanthroline)$_2$(4,4'-dicarboxylic acid-2,2'-bipyridine)]$^{2+}$, [Ru(4,7-diphenyl-1,10-phenanthroline)$_2$(4-methyl,4'-carboxylic acid-2,2'-bipyridine)]$^{2+}$, [Ru(4,7-diphenyl-1,10-phenanthroline(SO$_3$Na)$_2$)$_2$(4,4'-dicarboxylic acid-2,2'-bipyridine)]$^{2+}$, [Ru(4,7-diphenyl-1,10-phenanthroline(SO$_3$Na)$_2$)$_2$(4-methyl,4'-carboxylic acid-2,2'-bipyridine)]$^{2+}$, and [Ru bis(2,2'-bipyridyl)(phenanthroline-maleamide)].

12. A method as defined by claim 11, wherein the metal in each said fluorescent metal-ligand complex contains a transition metal.

13. A method as defined by claim 11, wherein the metal in each said fluorescent metal-ligand complex is selected from the group consisting of Co, Cr, Cu, Mo, Ru, Rh, W, Re, Os, Ir, and Pt.

14. A method as defined by claim 13, wherein the metal in each said fluorescent metal-ligand complex is selected from the group consisting of Ru, Os, Re, Rh, Ir, W, and Pt.

15. A method as defined by claim 14, wherein the metal in each said fluorescent metal-ligand complex is selected from the group consisting of Ru, Os, and Rh.

16. A method as defined by claim 15, wherein the metal in each said fluorescent metal-ligand complex is Os.

17. A method as defined by claim 11, wherein said fluorescent metal-ligand complex is selected from the group consisting of [Ru(2,2'-bipyridyl)$_2$(1,10-phenanthroline-9-isothiocyanate)]$^{2+}$, [Ru(4,7-diphenyl-1,10-phenanthroline)$_2$(4,4'-dicarboxylic acid-2,2'-bipyridine)]$^{2+}$, [Ru(4,7-diphenyl-1,10-phenanthroline)$_2$(4-methyl,4'-carboxylic acid-2,2'-bipyridine)]$^{2+}$, [Ru(4,7-diphenyl-1,10-phenanthroline(SO$_3$Na)$_2$)$_2$(4,4'-dicarboxylic acid-2,2'-bipyridine)]$^{2+}$, [Ru(4,7-diphenyl-1,10-phenanthroline(SO$_3$Na)$_2$)$_2$(4-methyl,4'-carboxylic acid-2,2'-bipyridine)]$^{2+}$, [Re(2,9-dimethyl-4,7-diphenyl-1,10-phenanthroline)(CO)$_3$(isonicotinic acid)]$^+$, [Ru bis(2,2'-bipyridyl)(phenanthroline-maleamide)], Bis(2,2'-bipyridine)(4,4'-dicarboxy-2,2'-bipyridine)osmium (II) hexafluorophosphate, Bis(2,2'-bipyridine)(4,4'-succidimidyl-2,2'-bipyridine)osmium (II) hexafluorophosphate, Bis(1,10-phenanthroline)(5-amino-1,10-phenanthroline)osmium (II), and (2,2',2"-terpyridine)(triphos)osmium (II).

* * * * *